(12) United States Patent
Perot et al.

(10) Patent No.: US 8,342,843 B2
(45) Date of Patent: Jan. 1, 2013

(54) DENTAL ARTICULATOR REFERENCE OBJECT

(75) Inventors: Jean-Marc Perot, Outremont (CA); Robin Provost, Montreal (CA)

(73) Assignee: Dental Wings, Inc., Montreal, Quebec (CA)

( * ) Notice: Subject to any disclaimer, the term of this patent is extended or adjusted under 35 U.S.C. 154(b) by 816 days.

(21) Appl. No.: 12/117,716

(22) Filed: May 8, 2008

(65) Prior Publication Data

US 2009/0280451 A1 Nov. 12, 2009

(51) Int. Cl.
*A61C 11/00* (2006.01)
(52) U.S. Cl. .......................... 433/213; 433/54
(58) Field of Classification Search .............. 433/54–68, 433/72–73, 24, 213–225, 34; 700/97–98, 700/118; 382/154; 702/150–153; 703/1; 356/620; 345/419–420
See application file for complete search history.

(56) References Cited

U.S. PATENT DOCUMENTS

| | | | |
|---|---|---|---|
| 5,957,688 A | 9/1999 | Van Valey | |
| 6,431,871 B1 | 8/2002 | Luthardt | |
| 6,450,809 B1 * | 9/2002 | Iverson | 433/64 |
| 2004/0172150 A1 * | 9/2004 | Perot et al. | 700/98 |
| 2007/0031791 A1 * | 2/2007 | Cinader et al. | 433/213 |
| 2007/0154867 A1 * | 7/2007 | Taub et al. | 433/213 |
| 2008/0002869 A1 | 1/2008 | Scharlack et al. | |

FOREIGN PATENT DOCUMENTS

| | | |
|---|---|---|
| DE | 10042109 | 3/2002 |
| WO | 2004030565 | 4/2004 |

\* cited by examiner

*Primary Examiner* — Yogesh Patel
(74) *Attorney, Agent, or Firm* — Anglehart et al.

(57) ABSTRACT

A dental model articulator of the type that has separable complementary articulation members is connected to a registration object having compatible complementary articulation members. The dental arches of each dental model articulator half is scanned with the reference object to give the axis of the articulator model. This facilitates generating a virtual dental model.

14 Claims, 3 Drawing Sheets

DENTAL ARTICULATOR REFERENCE OBJECT

TECHNICAL FIELD

The present invention relates to the manufacture of dental prosthetics, and more specifically to scanning of a dental model for the purposes of designing or manufacturing dental prosthetics, as well as the building of a virtual dental model.

BACKGROUND

A dental articulator assists in the fabrication of removable prosthodontic appliances (dentures), fixed prosthodontic restorations (crowns, bridges, inlays and onlays) and orthodontic appliances. In the fabrication of dental prosthetics, a negative impression is made of the teeth of a dental patient using a plastic material. The negative impression is then filled with a hardenable material to form a die. The die is affixed to a base formed of similar hardenable material to form a dental model. A dental model articulator is used to correlate upper and lower dental models in the forming and adjustment of the dental prosthesis.

The model is used by a technician to determine the optimum shape and position for the prosthetic to work in conjunction with the patient's other teeth and normal jaw motion. The articulator is important because it replicates the basic pivot action of the upper and lower mandibles, as well as translational motions. A prosthetic can then be inserted into the model to confirm that its proposed design and intended installed position should work properly in the patient's mouth, before placement of the prosthetic in the patient's mouth. In some cases, the model may be used to prepare a template or a guide to help the dentist place the implant and/or prosthetic in the patient's mouth.

Examples of commonly used articulators are commercially available from Dentsply Ceramco (the Vertex® product) and Orbix Dental Products (U.S. Pat. No. 5,957,688).

CAD/CAM dentistry (Computer-Aided Design and Computer-Aided Manufacturing in dentistry) is an area of dentistry utilizing an imaging camera, a computer, and a mill to produce fixed dental prosthetics, such as dental crowns and bridges. In CAD/CAM dentistry, the dental model is scanned, and the prosthetic is designed within software. To scan a dental model, the upper model and the lower model are scanned separately. These two half models must be registered to create a complete virtual dental model. Registration is done virtually or by scanning the models with the articulator to obtain by scan the necessary registration and articulation axis information.

SUMMARY

In this specification, "dental model articulator" is used to mean what is commonly referred to as an articulator (anatomical or adjustable) or an occlusor, namely whether a single or multiple degrees of freedom are provided.

It has been discovered that commonly used disposable articulators whose hinge mechanisms permit separation of the upper and lower dental arches can receive at their hinge mechanisms a reference object having a predetermined alignment with the articulator axis, so that such a reference object can be scanned with each dental arch to provide reference information for creating a virtual dental model including he necessary registration and articulation axis information from the dental model.

A dental model articulator of the type that has separable complementary articulation members is connected to a registration object having compatible complementary articulation members. The dental arches of each dental model articulator half is scanned with the reference object to give the axis of the articulator model. This facilitates generating a virtual dental model.

BRIEF DESCRIPTION OF THE DRAWINGS

The invention will be better understood by way of the following detailed description of embodiments of the invention with reference to the appended drawings, in which.

DETAILED DESCRIPTION

Figure 1:
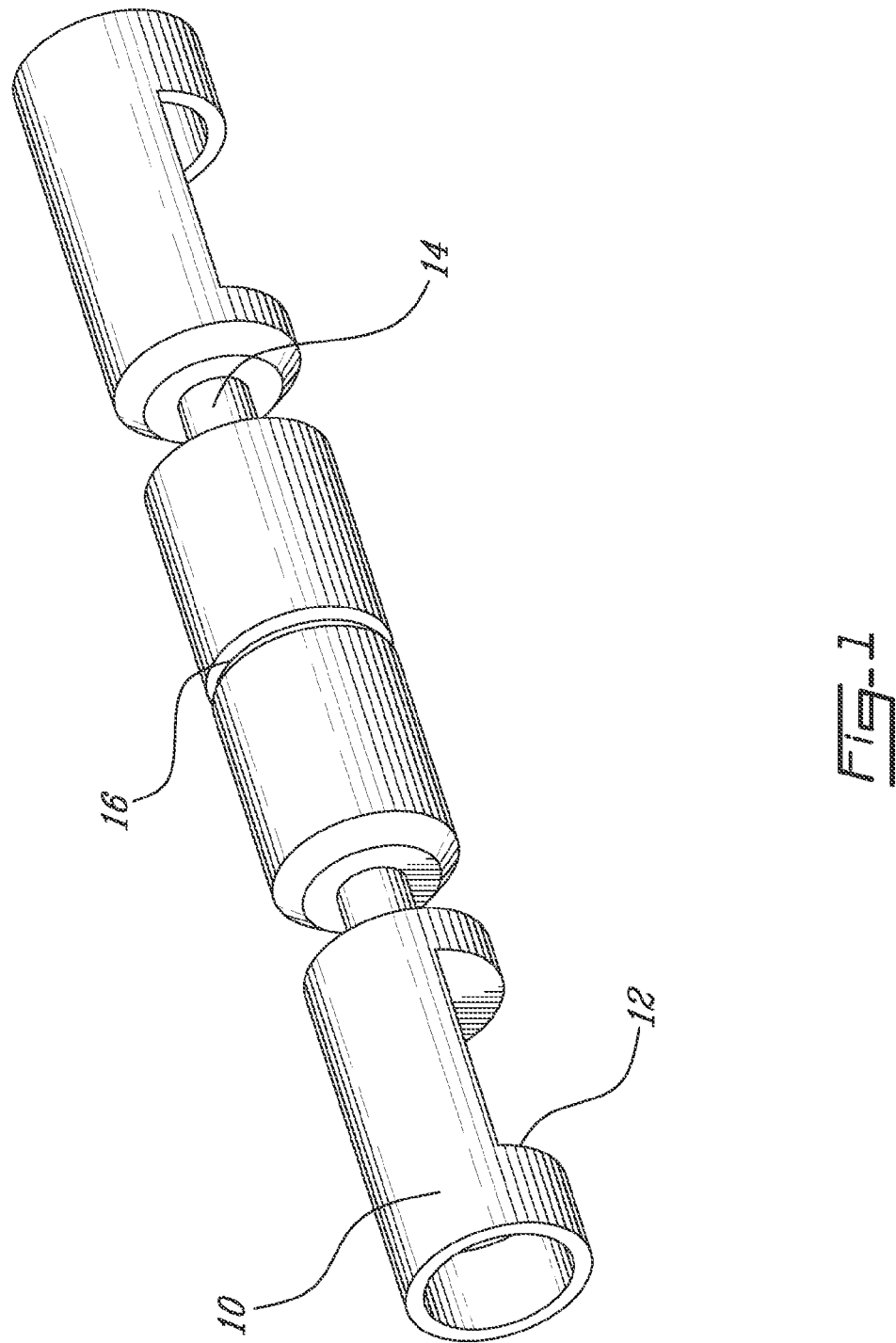
FIG. 1 is an oblique view of a reference object according to an embodiment of the invention.
Figure 2:
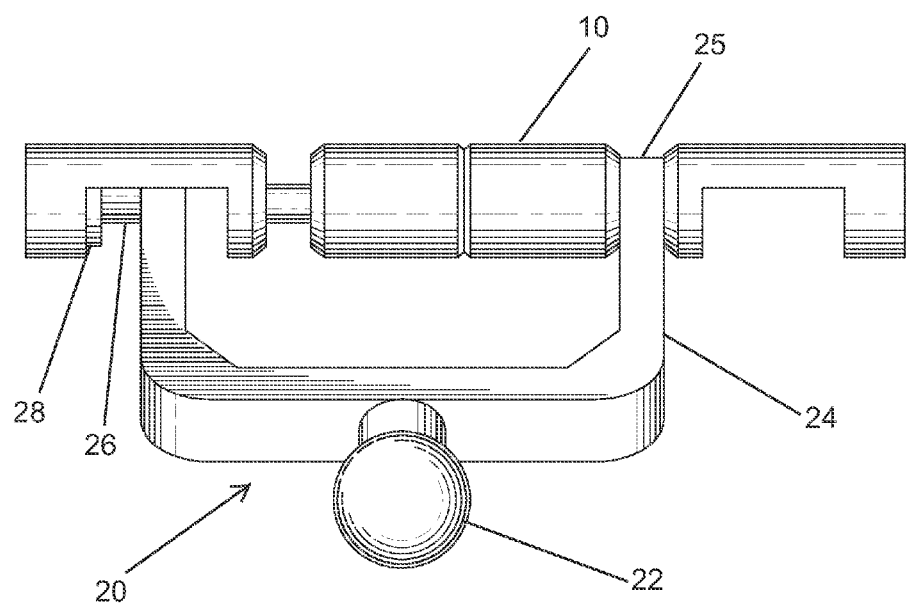
FIG. 2 is a perspective view of the reference object of FIG. 1 attached to a Vertex® articulator.

The reference object 10 illustrated in FIGS. 1 and 2 is designed to be used with the Vertex® articulator 20. The Vertex articulator 20 has a universal ball joint 22 at the bottom of a fork 24. At the top of the fork 24, each member has one side ending with a C-clip 25 and the other side with a laterally extending cylindrical shaft 26 ending in a wider disk 28, the disk 28 preventing the corresponding C-clip 25 from sliding on the shaft portion 26. Two like articulator members can be snapped together with C-clips engaging the corresponding shafts. The reference object 10 thus has a recess 12 snugly receiving the wider disk of the articulator 20, and a cylindrical shaft portion 14 with the suitable spacing between structures 12 and 14 to mate with the Vertex articulator 20 (see FIG. 2).

The reference object 10 can be made of any suitable material, and in the embodiment illustrated it is made of brushed aluminum that reduces specular reflection. In the embodiment illustrated, there is shown a central circumferential groove 16 that can be identified in the scan and used as a center reference mark. Alternatively, the ends of the object or other features can be used to identify from the reference object the important features, namely the axis and the center of the reference object that is the same as that of the articulator 20.

While not essential, the reference object shown is entirely symmetric and has two recesses 12 and two shaft portions 14 so that it can be snapped onto the articulator without concern for its own orientation.

Figure 3:
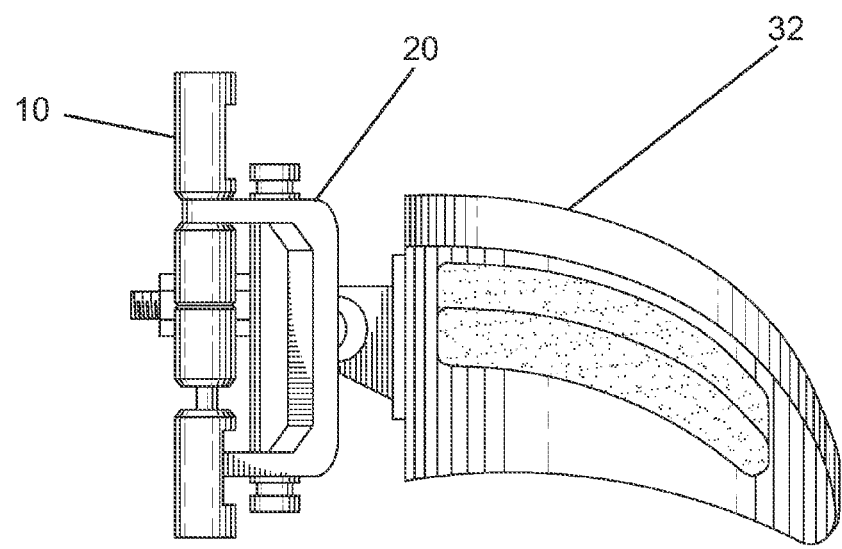
FIG. 3 is a top view of two dental model halves in their disconnected state placed on a scanner stage with the reference object inserted in the articulators.
Figure 3:
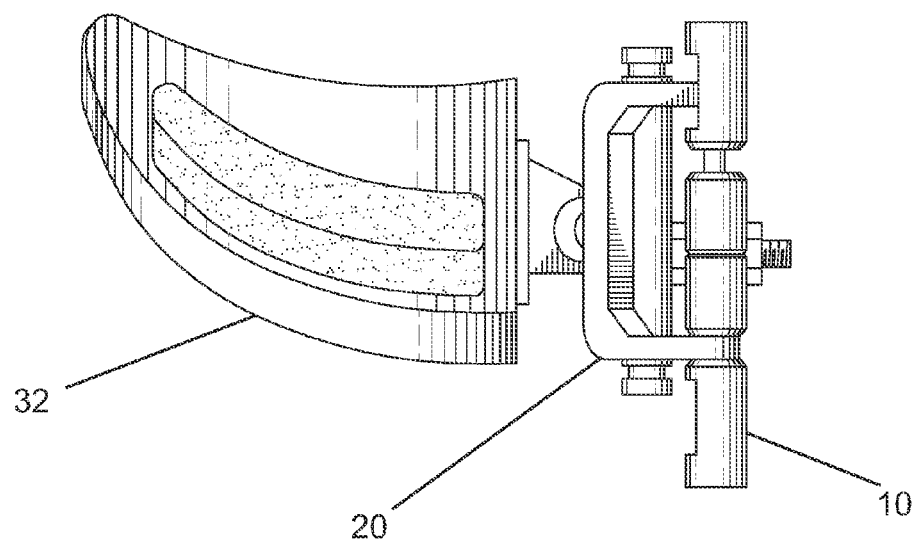

As shown in FIG. 3, the dental model 32 and articulator halves 20 with the reference object 10 snapped thereto can be scanned two at a time on a 3D scanner stage. It is not necessary when using the reference object 10 to scan the dental models 32 connected together with the articulator to obtain the desired registration and articulation axis information from the dental model 32.

To generating a virtual dental model, a physical mold model 32 is scanned by attaching the reference object 10 to articulation or hinge members of each one of the two dental model articulator 20 halves of the physical model 32. The object 10 will thus provide a reference of an articulation axis of the articulator 20. Then, each dental arch of the physical model 32 is scanned along with the reference object 10. A virtual dental model is built in software in a computer using information from the scanning of the dental arches and the reference object 10 to include articulation information in the virtual dental model. The building of a virtual dental model from scans of a physical dental model with reference or registration information relating the upper and lower dental arches is known in the art.

It will be appreciated that the registration object 10 will take a different form to mate with a different articulator 20. If an articulator 20 has distinct members for upper and lower arches, then it would follow that distinct reference objects 10 could be used.

What is claimed is:

1. A method of generating a virtual dental model from scanning a physical mold model, the method comprising:
    attaching a reference object to articulator members of each one of two dental model articulator halves of the physical model to provide a reference of an articulation axis of the articulator, wherein the reference object comprises a recess and a cylindrical shaft portion;
    scanning a dental arch mounted on one of said two dental model articulator halves of the physical model with the reference object; and
    building with a computer the virtual dental model using information from the scanning of the dental arch and the reference object to include articulation information in the virtual dental model.

2. The method as defined in claim 1, wherein said scanning comprises scanning each dental arch mounted on one of said two dental model articulator halves of the physical model with the reference object together in a single scan.

3. The method as defined in claim 1, wherein said scanning of the dental arches is scanning of the dental arches that are not connected together.

4. The method as defined in claim 1, wherein the articulator members comprise a unit having a first member and a second member different from said first member and sharing a common axis of pivot, wherein said first member of one articulator half is adapted to mate with said second member of another articulator half as compatible complementary articulator members, said compatible complementary articulator members comprise two complementary first members and two complementary second members arranged to allow said reference object to connect to said unit without regard to orientation of said reference object.

5. The method as defined in claim 4, wherein the first member has an end that is a C-clip and the second member has an end that is a laterally extending cylindrical shaft with a disk that is adapted to prevent a corresponding C-clip from sliding on the shaft portion.

6. The method as defined in claim 1, wherein said reference object is essentially cylindrical.

7. The method as defined in claim 1, wherein said reference object comprises a center marking.

8. A method of generating a virtual dental model from scanning a physical mold model having two dental model articulator halves, each one of said articulator halves comprising complementary articulator members connectable together for pivoting about an articulation axis of the articulator, the method comprising:
    providing said two dental model articulator halves connected together with respect to said articulation axis;
    separating said two dental model articulator halves;
    attaching a reference object to articulator members at said articulation axis of each one of said two dental model articulator halves to provide a reference of an articulation axis of the articulator, wherein the reference object comprises a recess and a cylindrical shaft portion;
    scanning with a scanner a dental arch mounted on one of said two dental model articulator halves of the physical model with the reference object; and
    building with a computer the virtual dental model using information from the scanning of the dental arch and the reference object to include articulation information in the virtual dental model.

9. The method as defined in claim 8, wherein said scanning comprises scanning each dental arch mounted on one of said two dental model articulator halves of the physical model with the reference object together in a single scan.

10. The method as defined in claim 8, wherein said building the virtual dental model is done without using information from scanning of the dental arches connected together.

11. The method as defined in claim 8, wherein the articulator members comprise a unit having a first member and a second member different from said first member and sharing a common axis of pivot, wherein said first member of one articulator half is adapted to mate with said second member of another articulator half as compatible complementary articulator members, said compatible complementary articulator members comprise two complementary first members and two complementary second members arranged to allow said reference object to connect to said unit without regard to orientation of said reference object.

12. The method as defined in claim 11, wherein the first member has an end that is a C-clip and the second member has an end that is a laterally extending cylindrical shaft with a disk that is adapted to prevent a corresponding C-clip from sliding on the shaft portion.

13. The method as defined in claim 8, wherein said reference object is essentially cylindrical.

14. The method as defined in claim 8, wherein said reference object comprises a center marking.

* * * * *